United States Patent
Nakajima et al.

(10) Patent No.: US 6,773,575 B2
(45) Date of Patent: Aug. 10, 2004

(54) ELECTROLYTIC CELL AND PROCESS FOR THE PRODUCTION OF HYDROGEN PEROXIDE SOLUTION AND HYPOCHLOROUS ACID

(75) Inventors: Yasuo Nakajima, Fujisawa (JP); Yoshinori Nishiki, Fujisawa (JP); Genzo Yamane, Fujisawa (JP); Masaharu Uno, Fujisawa (JP); Akira Katsumoto, Osaka (JP); Kunio Nishimura, Osaka (JP)

(73) Assignees: Permelec Electrode Ltd., Kanagawa (JP); Katayama Chemical, Inc., Osaka (JP)

(*) Notice: Subject to any disclaimer, the term of this patent is extended or adjusted under 35 U.S.C. 154(b) by 211 days.

(21) Appl. No.: 10/103,034

(22) Filed: Mar. 22, 2002

(65) Prior Publication Data
US 2002/0134687 A1 Sep. 26, 2002

(30) Foreign Application Priority Data
Mar. 23, 2001 (JP) .................................... P. 2001-085533

(51) Int. Cl.[7] .......................... C02F 1/461; C25B 1/30
(52) U.S. Cl. .................... 205/466; 205/556; 205/746; 205/756; 204/263; 204/265
(58) Field of Search .............................. 205/466, 556, 205/746, 756; 204/263, 265

(56) References Cited

U.S. PATENT DOCUMENTS

| 5,647,968 | A | * | 7/1997 | Fraser et al. ................. 205/466 |
| 5,997,717 | A | * | 12/1999 | Miyashita et al. ........... 205/466 |
| 6,113,773 | A | * | 9/2000 | Shimamune et al. ........ 205/466 |
| 6,547,947 | B1 | * | 4/2003 | Uno et al. .................... 205/466 |

* cited by examiner

Primary Examiner—Arun S. Phasge
(74) Attorney, Agent, or Firm—Sughrue Mion, PLLC

(57) ABSTRACT

An electrolytic cell and process for the simultaneous production of hydrogen peroxide and hypochlorous ion. The electrolytic cell has an anode chamber housing an insoluble anode capable of oxidizing halide ion, a cathode chamber housing a gas diffusion cathode capable of oxidizing an oxygen-containing gas to produce hydrogen peroxide, a membrane separating the anode and cathode chambers, and means for supplying water containing halide ion to the anode chamber and an oxygen-containing gas and an electrolyte to the cathode chamber, whereby hypohalide and hydrogen peroxide are produced in the anode chamber and the cathode chamber, respectively. Also disclosed is a process for treating water using the electrolytic cell.

12 Claims, 2 Drawing Sheets

ELECTROLYTIC CELL AND PROCESS FOR THE PRODUCTION OF HYDROGEN PEROXIDE SOLUTION AND HYPOCHLOROUS ACID

FIELD OF THE INVENTION

The present invention relates to a process for the electrolysis of an electrolyte such as seawater which comprises the simultaneous production of hydrogen peroxide and hypohalide to efficiently produce an aqueous solution containing both of these chemicals.

BACKGROUND OF THE INVENTION

Due to concern that air pollution and deterioration of water quality of rivers and lakes caused by industrial and household wastes can have adverse effects on the environment and human body, technical countermeasures for solving these problems are in urgent demand. In the treatment of drinking water, sewage and waste water, it has been the practice to add a chemical such as chlorine to decolor and sterilize the water to be treated and reduce the COD thereof. However, since the addition of a large amount of chlorine causes the production of harmful materials, i.e., environmental hormones (extrinsic incretion disturbing material) and carcinogenic substances, the recent trend is to add less chlorine added.

Further, under some combustion conditions, the incineration of waste can cause the production of carcinogenic substances (dioxins) which affect the ecosystem and thus has been noted as a safety problem. In order to solve the problems of water treatment, the following processes have been proposed as a substitute for the addition of chlorine.

An electrolysis process utilizes clean electrical energy to control chemical reaction on the surface of electrodes, thereby producing hydrogen, oxygen, ozone, hydrogen peroxide, etc. Thus, the material to be treated can be indirectly decomposed. Alternatively, the material to be treated can be adsorbed to the electrodes where it is directly subjected to electrolysis. An electrolysis process has heretofore been utilized for the treatment of waste water.

Hydrogen peroxide is useful as a fundamental chemical indispensable for treatment in the fields of food, medicine, pulp, fiber and semiconductors in addition to water treatment. In particular, noted future uses include the cleaning of electronic parts and sterilization of medical equipment and facilities. At present, hydrogen peroxide is produced in large amount by an anthraquinone process. The electrolytic production of hydrogen peroxide making best use of the advantage of the electrolysis process has been studied and commercially practiced.

In the electrolysis of water, the cathode reaction normally involves the production of hydrogen. When oxygen is present in the cathode chamber, the reduction of oxygen preferentially proceeds. Thus, by controlling chemical reaction on the surface of the cathode, hydrogen peroxide is produced. This electrolysis process allows on-site production of hydrogen peroxide, eliminating the danger in prolonged storage with a stabilizer and transportation or the necessity of anti-pollution measures. With respect to the on-site electrolytic production of hydrogen peDRoxide, if seawater is used as an electrolyte, seawater containing hydrogen peroxide is obtained.

Referring to the production of hydrogen peroxide by electrolysis, various electrolytic processes are described for comparison in *Journal of Applied Electrochemistry*, Vol. 25, 613-(1995). All these processes allow for efficient production of hydrogen peroxide in an atmosphere of an alkaline aqueous solution and thus require the supply of an alkaline aqueous solution as a starting material. Thus, an aqueous solution of an alkali such as KOH and NaOH is essential. The decomposition of formaldehyde by hydrogen peroxide is described in *Journal of the Electrochemical Society*, Vol. 140, 1,632-(1993). *Journal of the Electrochemical Society*, Vol. 141, 174-(1994), proposes a method which comprises electrolysis of purified water as a starting material using an ion exchange membrane wherein ozone and hydrogen peroxide are synthesized at the anode and the cathode, respectively. However, this method has a low current efficiency and thus is not practical. It has been reported that a similar method can be effected under high pressure to raise the current efficiency. However, this proposal, too, is not practical from the standpoint of safety. An electrolysis process using a palladium foil has also been proposed. However, this electrolysis process is limited in its use because it can produce hydrogen peroxide only in a low concentration and adds to cost.

In the conventional electrolysis of seawater, the production of THM (trihalomethanes) from organic material which is unavoidably present in seawater restricts the use of the resulting seawater having a sterilizing effect and has an adverse effect on the environment.

It is known that when an aqueous solution containing halide ion such as seawater is subjected to electrolysis as an anolyte, a hypohalide is produced. This seawater containing hypohalide has a strong sterilizing effect and thus is used to kill bacteria in the seawater.

On the other hand, it has been reported that when hypohalide ion is added to seawater containing hydrogen peroxide, the oxidizing power of the seawater is enhanced (Japanese Patent Laid-Open No. 1996-24870). It is disclosed in the above cited patent publication that when effective chlorine such as hypohalide is added to seawater having a hydrogen peroxide content of 0.01 mg/l to an extent such that no trihalomethane (THM) is produced, seawater having a sterilizing power is produced. However, since hydrogen peroxide, which is a starting material, must be transported from the production site to a remote site where it is used, problems of safety, etc., remain.

SUMMARY OF THE INVENTION

It is therefore an object of the invention to provide an electrolytic cell and process for the simultaneous production of hydrogen peroxide and hypochlorous ion, which have heretofore been produced separately.

The foregoing objects of the invention will become apparent from the following detailed description and Examples.

The invention provides an electrolytic cell and process for the production of hydrogen peroxide solution and hypohalide by electrolysis which comprises an anode chamber housing an insoluble anode capable of oxidizing halide ion, a cathode chamber housing a gas diffusion cathode capable of oxidizing an oxygen-containing gas to produce hydrogen peroxide, a membrane separating the anode and cathode chambers, and means for supplying water containing halide ion to the anode chamber and oxygen-containing gas and an electrolyte to the cathode chamber, whereby hypohalide and hydrogen peroxide are produced in the anode chamber and the cathode chamber, respectively. The electrolyte, particularly anolyte supplied to the electrolytic cell, is preferably seawater which has previously been freed of organic material. Further, the catholyte containing hydrogen peroxide thus obtained and the anolyte containing hypochlorous ion may be added to water to be treated upstream and downstream of the electrolytic cell, respectively, making it possible to efficiently treat the water.

BRIEF DESCRIPTION OF THE DRAWINGS

By way of example and to make the description more clear, reference is made to the accompanying drawings in which.

DETAILED DESCRIPTION OF THE INVENTION

Figure 1:
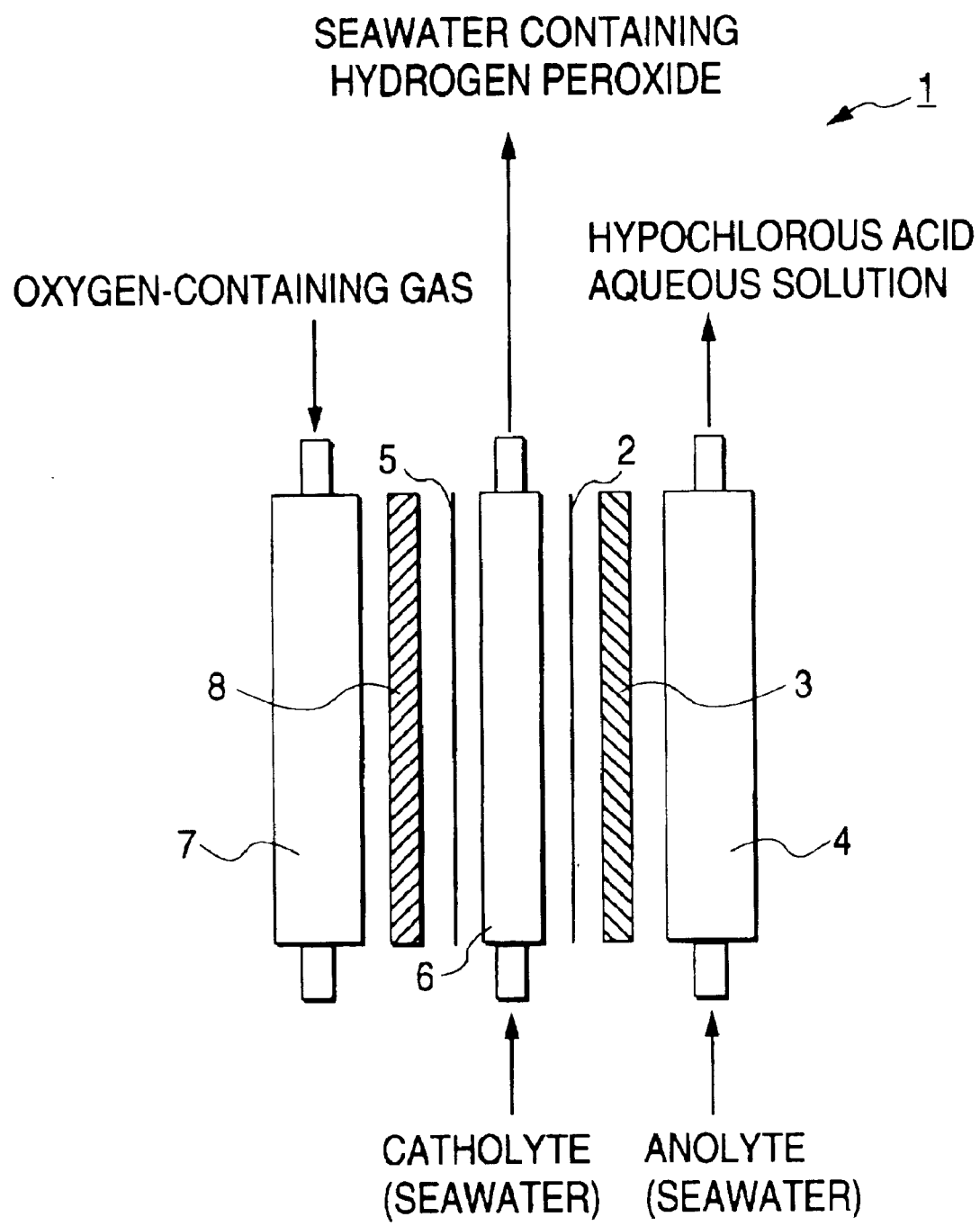
FIG. 1 is an exploded longitudinal sectional view illustrating the electrolytic cell employable in the process of the invention.

The invention will be described in detail below.

Unlike conventional processes for the electrolysis of seawater involving the separate production of hydrogen peroxide solution and halide ion, the invention provides for the simultaneous production of hydrogen peroxide solution and halide ion in a single electrolysis operation. In an on-site electrolysis process using seawater as an electrolyte, these two products can be simultaneously produced from seawater as a starting material.

When hydrogen peroxide or a hypohalide is singly produced by electrolysis as in a conventional process, the required power cost is about twice that consumed by the apparatus and process of the invention. Other costs of electrolysis, too, are much greater than that of the apparatus and process of the invention, but not as much as twice that of the invention. In the invention, the material of the electrode and the electrolysis conditions are properly predetermined so that hydrogen peroxide and a hypohalide can be simultaneously produced, making it possible to remarkably reduce the power cost and related costs.

In an embodiment where both hydrogen peroxide and a hypohalide are produced on-site, the two chemicals, which are dangerous and troublesome in transportation, can be used to treat seawater or for other purposes substantially without being transported, making it possible to considerably enhance treatment efficiency.

In the invention, the seawater supplied to the electrolytic cell is preferably freed of organic material.

The total organic carbon content (TOC) in seawater is about 10 ppm, and depends on the site where it is collected.

Regulations on trihalomethane compound in public water area have been established to eliminate effects thereof on the human body and living body. For example, the maximum allowable concentration of trichloroethylene and tetrachloroethylene are 0.03 mg/l and 0.01 mg/l, respectively. It is thus difficult to limit the concentration of THM produced by the reaction of organic (TOC) components in seawater with chlorine gas or hypochlorous acid produced by electrolysis or by direct electrolytic oxidation reaction of an effective chlorine component with organic carbon components to an amount not greater than the standard.

When seawater having a TOC of about 10 ppm is subjected to electrolysis, chlorine gas or hypochlorous acid produced by the oxidation of chloride ion chlorinates an organic material to produce THM. Accordingly, conventional electrolysis processes which comprise effecting electrolysis while supplying seawater to the anode chamber and cathode chamber to obtain a hydrogen peroxide solution are unavoidably subject to the production of effective chlorine in the anode chamber, in which electrolytic oxidation occurs, and THM by the chlorination of organic material by the effective chlorine.

On the contrary, in a preferred embodiment of the invention, the electrolyte, particularly seawater supplied into the electrolytic cell, is freed of organic material to minimize the concentration of organic material in the electrolyte of the electrolytic cell, thereby avoiding the oxidation reaction of organic material in the anode chamber, which causes the production of THM.

Examples of techniques for removing organic material from seawater include removal by a strainer, cohesive separation, adsorption by activated charcoal, oxidative destruction by ultraviolet ray, ozone, hydrogen peroxide, electrolysis or the like, and biodegradation. These means may be selected depending on the quality of the water to be treated, etc.

In order to treat flowing water, and particularly to remove THM from the water to be treated, the catholyte containing hydrogen peroxide and the anolyte containing hypohalide may be added to the water to be treated upstream and downstream of the electrolytic cell, respectively, to facilitate treatment.

In the electrolytic cell for use in the process of the invention, a hypohalide and hydrogen peroxide are produced on the anode chamber side and on the cathode chamber side, respectively.

The anode for use in the invention is an insoluble anode. The insoluble anode eliminates disadvantages of installation of a gas diffusion electrode and the supply of dangerous hydrogen gas accompanying use of the hydrogen gas anode. The cathode for use in the invention is an oxygen gas diffusion cathode which efficiently produces hydrogen peroxide by the reduction of oxygen gas.

The catalyst for the oxygen gas electrode is preferably a metal such as gold, an oxide thereof or carbon such as graphite and electrically conductive diamond. The oxygen gas electrode may have an organic material such as polyaniline and thiol (organic compound containing—SH group) coated thereon. Such a catalyst may be used in sheet form or porous form. Alternatively, the catalyst may be supported on a plate, metal gauge, sintered powder or sintered metal fiber of a corrosion-resistant material such as stainless steel, zirconium, silver and carbon in an amount of from 1 to 1,000 g/m$^2$ by a thermal decomposition method, resin fixing method, composite plating method or the like. By forming a hydrophobic sheet on the side of the cathode opposite the anode, the supply of gas to the reactive surface can be controlled to advantage.

The cathodic current corrector for use in the present invention is a metal such as carbon, nickel, stainless steel and titanium or alloy or oxide thereof preferably in a porous or sheet form. In order to smoothly supply and withdraw reaction product gas and electrolyte, a hydrophilic or hydrophobic material is preferably supported in dispersion on the surface of the electric supplier.

When the electrical conductivity of the catholyte is low, it raises the cell voltage or shortens the life of electrode. In this case, the electrolytic cell is preferably arranged such that the oxygen gas diffusion cathode is positioned as close as possible to the ion exchange membrane (the width of the solution chamber is reduced) for the purpose of inhibiting contamination by the material of gas electrode and other purposes.

The amount of oxygen supplied to the cathode is preferably from the same as to about twice the theoretical value. The oxygen source may be air, a commercially available oxygen cylinder, oxygen produced by the electrolysis of water in a separately installed electrolytic cell or oxygen obtained by concentrating air by a PSA (pressure swing adsorption) device. In general, as the oxygen concentration is increased, a hydrogen peroxide solution can be produced at a higher current density.

The use of a membrane separating the anode chamber and the cathode chamber makes it possible to retain the active material produced by the electrode reaction away from the counter electrode and to accelerate electrolysis even if the electrical conductivity of the electrolyte is low. The membrane may be a neutral membrane or an ion exchange membrane. In particular, an anion exchange membrane is preferred to prevent the oxidation of halide ion on the anode. The membrane may be made of a fluororesin or a hydrocarbon-based material. From the standpoint of corrosion resistance, the former material is preferred. A commercially available particulate ion exchange resin may be used as a solid porous material having an ion exchange capacity. Examples of the hydrocarbon-based resin for use herein include styrene resin, acrylic resin, and aromatic resin. From the standpoint of corrosion resistance, a fluorine-based ion exchange resin is preferred. Alternatively, a component having an ion exchange capacity may be formed on a suitable porous supporting member. The porosity of such a material is preferably from 20% to 90% taking into account the uniform dispersion of solution and resistivity. The size of pores or the size of the particulate material is preferably from 0.1 to 10 mm.

For providing stability, the anode catalyst may be a noble metal such as iridium, platinum and ruthenium or a composite oxide comprising an oxide thereof and an oxide of a valve metal such as titanium and tantalum. Alternatively, a carbon-based material such as graphite and electrically conductive diamond may be used.

Referring to the electrolysis conditions, the solution temperature is preferably from 5° C. to 60° C., and the current density is preferably from 0.1 to 100A/dm$^2$. The distance between the electrodes should be reduced to lower the resistance loss. The distance between the electrodes is preferably from 1 to 50 mm to reduce the pressure loss of the pump for supplying the electrolyte and to keep the pressure distribution uniform.

The electrolytic cell is preferably made of a glass lining material, carbon, or corrosion-resistant titanium, stainless steel or PTFE resin from the standpoint of durability and stability of hydrogen peroxide.

The concentration of hydrogen peroxide thus produced can be controlled to a range of from 10 ppm to 10,000 ppm (1% by weight) by adjusting the amount of water supplied to the electrolytic cell and the current density.

When seawater is electrolyzed, hydroxides or carbonates of calcium or magnesium are gradually deposited on the surface of the cathode. In order to remove these salts, preferably the electrolytic cell is regularly washed with hydrochloric acid or a chelating agent is regularly injected into the electrolytic cell.

A preferred embodiment of the electrolytic cell for use in the process of the invention for the production of hydrogen peroxide and hypohalide will be described in detail in connection with FIGS. 1 and 2.

FIG. 1 is an exploded longitudinal sectional view illustrating an embodiment of the electrolytic cell suitable for the process of the invention for the production of seawater containing hydrogen peroxide and hypohalide. FIG. 2 is a flow chart illustrating the production process of FIG. 1.

Figure 2:
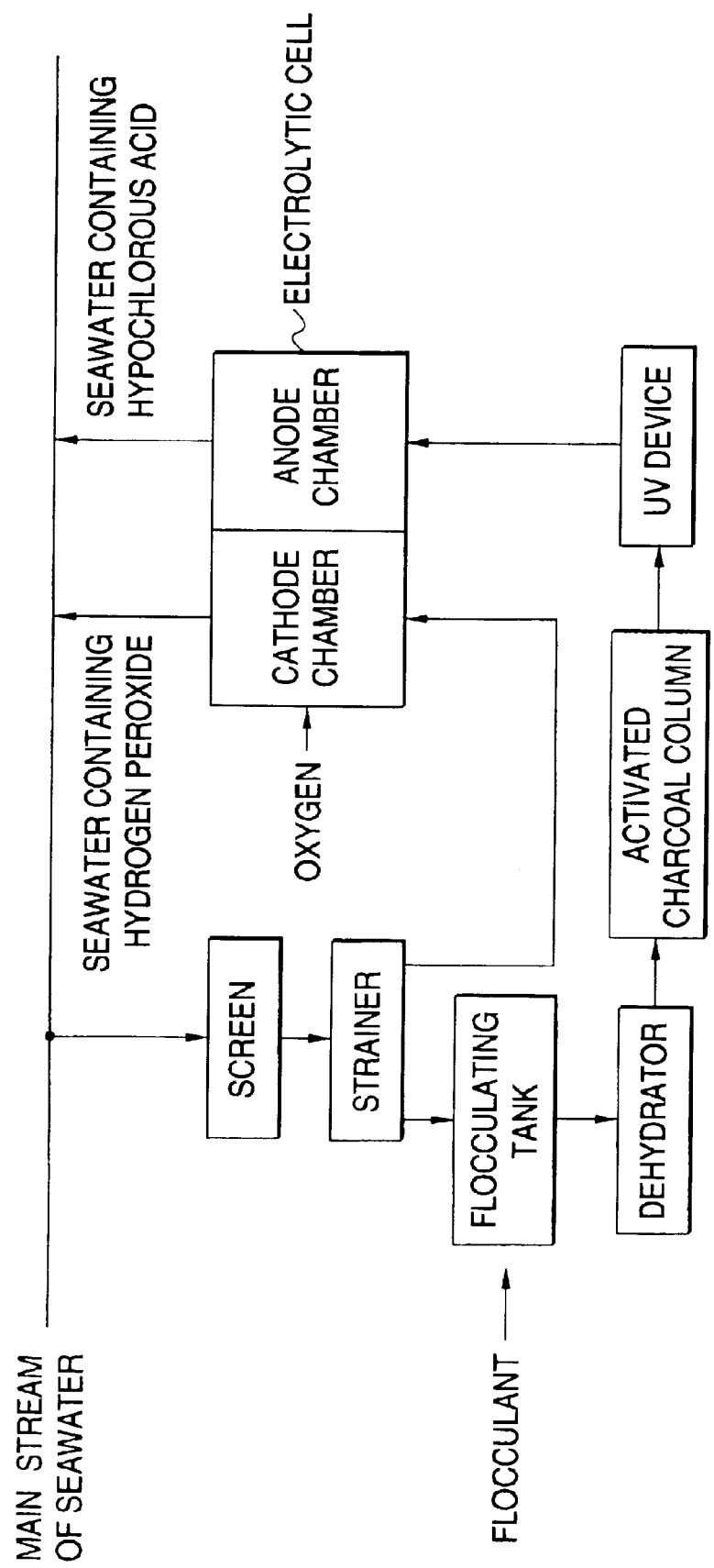
FIG. 2 is a flow chart illustrating the process for the treatment of seawater in Example 1, wherein the reference numeral 1 indicates an electrolytic cell, the reference numeral 2 indicates a cation exchange membrane, the reference numeral 3 indicates an anode, the reference numeral 4 indicates an anode chamber, the reference numeral 5 indicates an oxygen gas electrode, the reference numeral 6 indicates a solution chamber, and the reference numeral 7 indicates a gas chamber.

As shown in FIG. 2, the main stream of the seawater is branched. The seawater thus branched is then treated by a screen and a strainer device to substantially remove large suspended matter therefrom. A flocculant is then added to a part of the seawater in an amount of from 10 to 10,000 ppm in a flocculating tank so that normally negatively charged suspended organic matter is neutralized by a polyvalent metal ion to undergo agglomeration. Subsequently, a polymer is added to the seawater in an amount of from 100 to 1,000 ppm to undergo flocculation and agglomeration. In general, the seawater is stirred for several hours to terminate the agglomeration reaction.

The flocculant may be a sulfate or chloride of iron or aluminum such as alum, sulfate band and polyaluminum chloride. The polymer may be a polyethyleneimine, polyacrylamide, sodium polyacrylate, gelatin, starch or sodium alginate. A polymer which specifically adsorbs COD may be used as well.

In this manner, the content of residual organic materials in the seawater can be reduced to a range of from 10 ppm to 100 ppm. Other surface active agents or flocculants may be added depending on the kind of seawater to be treated.

The agglomerate thus separated is preferably then subjected to sedimentation or suspension. Taking into account post-treatment, the agglomerate is preferably subjected to treatment by a dehydrator so that it is divided into seawater and agglomerate. Subsequently, the seawater is treated in an activated charcoal column so that low molecular organic material is adsorbed leaving a content of from 0.1 to 10 ppm. Zeolite or activated alumina may be used instead of activated charcoal.

Low molecular organic materials which still remain after this procedure are then irradiated with ultraviolet rays in an ultraviolet device. The irradiation with ultraviolet rays may be replaced by or accompanied by treatment with ozone or hydrogen peroxide or electrical separation.

The seawater thus treated is then supplied to the anode chamber of the electrolytic cell described below.

The seawater which has been treated in the strainer device is then partly supplied to the cathode chamber as shown in FIG. 2.

The electrolytic cell 1 is a two chamber type electrolytic cell which is partitioned by a cation exchange membrane 2 into an anode chamber 4 having an anode 3 in the form of a porous sheet and a cathode chamber. An oxygen gas electrode 5 is used as the cathode. The oxygen gas electrode 5 partitions the cathode chamber into a solution chamber 6 on the cation exchange membrane side and a gas chamber 7 on the opposite side.

The anode chamber 4 is supplied with seawater which preferably has been previously freed of organic material as described above. The chloride ion (Cl$^-$) in the seawater thus supplied is then anodically oxidized to hypochlorous ion (ClO$^-$).

Electric current is supplied to the oxygen gas electrode from a porous electric supplier 8 disposed in close contact with the back side thereof. An oxygen-containing gas such as oxygen gas is supplied through an oxygen gas feed pipe disposed on the back side of the oxygen gas electrode 5. The oxygen-containing gas thus supplied passes through the oxygen gas electrode 5. During this process, the oxygen-containing gas is partly reduced by the electrode catalyst to hydrogen peroxide and then reaches the solution chamber 6. On the other hand, seawater which has or has not been freed of organic compounds is supplied to the solution chamber 6. Hydrogen peroxide produced by the oxygen gas electrode 5 is dissolved in the seawater in the solution chamber 6 to provide a hydrogen peroxide solution which is then withdrawn from the electrolytic cell 1 through a hydrogen peroxide outlet pipe.

In this manner, the cathode chamber produces seawater containing hydrogen peroxide free of effective chlorine and organic halogen compound while the anode chamber produces an aqueous solution of hypochlorous acid.

The lower limit of the amount of hydrogen peroxide to be added to seawater which can inhibit the proliferation of organisms in the seawater is about 1 ppm. Since the concentration of hydrogen peroxide in the seawater containing hydrogen peroxide obtained by the electrolysis of seawater freed of organic material is as high as about 1,000 ppm, the seawater thus obtained may be diluted about 1,000 times for the treatment of seawater. Accordingly, in an embodiment where organic material is removed from the seawater supplied to the electrolytic cell, the concentration of THM in the seawater actually treated can be kept to a maximum level of not greater than 0.1 ppb. The effect of introducing the electrolytic cell on the desired quality of the seawater to be treated is negligible.

When the seawater withdrawn from the electrolytic cell contains organic material in an amount of about 10 ppm and the amount of the seawater to be treated is 1,000 $m^3/hr$, the amount of seawater directed to the electrolytic cell is only 1 $m^3/hr$. Thus, the amount of organic material in the seawater is about 10 g/hr, which hardly deteriorates the quality of the seawater. On the other hand, since the amount of the chemical to be added to flocculate the organic materials is 10 times the amount of organic materials at maximum and the amount of flocculated material separated as a solid material is about 100 g/hr, the treatment is not troublesome.

Examples of the process of the invention for the production of hydrogen peroxide solution will be described hereinafter, but the invention should not be construed as being limited thereto.

EXAMPLE 1

An iridium oxide catalyst was supported on a porous titanium sheet in an amount of 10 $g/m^2$ by a thermal decomposition method to prepare an anode.

A carbon powder (Type XC-72 furnace black, produced by Vulcan Inc. of U.S.A.) as a catalyst was kneaded with a PTFE resin. The mixture was applied to a carbon cloth (produced by Nippon Carbon Co., Ltd.), and then calcined at a temperature of 330° C. to prepare a sheet having a thickness of 0.4 mm as an oxygen gas electrode.

The above anode was placed in close contact with an ion exchange membrane (Nafion 117, produced by Du Pont Inc.). The above oxygen gas electrode was disposed such that the distance between the electrodes was 5 mm. As a result, an electrolytic cell shown in FIG. 1 having an effective electrolysis area of 20 $cm^2$ and comprising an anode chamber and a cathode chamber (solution chamber and gas chamber) was assembled.

A screen (interlattice space: 1 mm) and a strainer device (resin filter having an interlattice space of 10 $\mu m$) were disposed upstream of the electrolytic cell. The seawater was passed through the screen and the strainer device to remove considerably large suspended matter therefrom. Ferric sulfate (flocculant) was then added to a part of the seawater in a concentration of 20 ppm. A polyethyleneimine (polymer) was then added to the part of the seawater in a concentration of 100 ppm. This seawater was stirred for 2 hours, and then allowed to stand for sedimentation. The seawater was then subjected to treatment by a dehydrator to separate the solid matter therefrom. The seawater thus obtained had an organic material concentration of about 1 ppm. The seawater was then passed through an activated charcoal column so that the organic material was adsorbed and reduced to a concentration of 0.1 ppm. The seawater was then irradiated with ultraviolet rays so that the organic material concentration was further reduced to 10 ppb. Thus, seawater substantially free of organic activity was obtained.

An electric current of 2A was passed through the anode and the cathode, while oxygen gas obtained from a PSA device, seawater filtrate treated to remove only considerably large diameter impurities and seawater having an organic compound concentration of 10 ppb were supplied to the gas chamber, the solution chamber of the cathode chamber and the anode chamber at a rate of 20 ml/min, respectively. As a result, seawater having a hydrogen peroxide content of 900 ppm was obtained at the outlet of the cathode chamber at a current efficiency of about 85%. Also, seawater having an effective chlorine concentration of about 1,800 ppm was obtained at the outlet of the anode chamber at a current efficiency of about 80% when the cell voltage was 8 V.

Under these conditions, the operation of the electrolytic cell continued for 200 hours. As a result, the current efficiency in the production of hydrogen peroxide and effective chlorine (hypochlorous ion concentration) were reduced to 80% and 75%, respectively, and the cell voltage rose to 9 V. However, electrolysis continued. The concentration of THM in the anolyte was 5 ppb.

The catholyte containing hydrogen peroxide thus obtained was injected into the seawater at the inlet of the seawater pipe such that the hydrogen peroxide concentration reached about 2 ppm, while anolyte containing hypochlorous ions was injected into the seawater at the central portion of the seawater pipe such that the hypochlorous ion concentration reached about 0.5 ppm. Under these conditions, the manner in which living bodies attach to and grow on the inner wall of the pipe was observed. As a result, no living bodies were observed attached to the inner wall of the pipe over the length thereof even after a month. The concentration of THM at the outlet of the pipe after a month fell below the limit of detection.

COMPARATIVE EXAMPLE

The electrolytic production of hydrogen peroxide and hypochlorous ions and the treatment of seawater by these chemicals were effected in the same manner as in Example 1, except that the seawater was not treated to reduce the organic material content. The concentration of organic material in the seawater thus used was about 5 ppm. The cell voltage was 8 V. Seawater having a hydrogen peroxide concentration of 900 ppm was obtained at the outlet of the cathode chamber at a current efficiency of about 95%. Seawater having an effective chlorine concentration of about 1,800 ppm was obtained at the outlet of the anode chamber.

Under these conditions, the operation of the electrolytic cell continued for 200 hours. As a result, the current efficiency in the production of hydrogen peroxide and effective chlorine (hypochlorous ion concentration) were reduced to 80% and 75%, respectively, and the cell voltage rose to 9 V. However, electrolysis continued. The concentration of THM in the anolyte was 4 ppm.

The catholyte and anolyte thus obtained in the foregoing electrolysis process were used to treat seawater in the same manner as in Example 1. As a result, no living bodies such as barnacles were attached to the inner wall of the pipe. The concentration of THM at the outlet of the pipe after a month was about 11 ppb.

The invention provides an electrolytic cell for the production of hydrogen peroxide solution and hypohalide by electrolysis, which comprises an anode chamber housing an insoluble anode capable of oxidizing halide ion, a cathode chamber housing a gas diffusion cathode capable of oxidizing an oxygen-containing gas to produce hydrogen peroxide, a membrane separating the anode and cathode chambers, and means for supplying water containing halide ion to the anode chamber and an oxygen-containing gas and an electrolyte to the cathode chamber, whereby hypohalide and hydrogen peroxide are produced in the anode chamber and the cathode chamber, respectively.

In the process of the invention, both hydrogen peroxide solution and hypohalide can be simultaneously produced by a single electrolysis operation. Unlike conventional processes, the process of the invention involves proper predetermination of the electrode material and electrolysis conditions for simultaneously producing hydrogen peroxide and hypohalide, making it possible to drastically reduce the power cost and related costs. In an embodiment where both hydrogen peroxide and a hypohalide are produced on-site, the two chemicals, which are dangerous and troublesome when transported, can be used to treat seawater or for other purposes substantially without being transported. This makes it possible to considerably enhance the treatment efficiency.

When seawater is used as an electrolyte, organic material contained therein is anodically oxidized to produce an organic halogen compound such as harmful THM. Accordingly, the seawater supplied to the anode chamber is preferably treated to remove organic matter.

On the contrary, even when the electrolyte supplied to the cathode chamber contains organic material, no THM is produced.

The anolyte containing hypochlide ion thus produced and the catholyte containing hydrogen peroxide can be used separately. In order to treat flowing water such as seawater from which the anolyte and the catholyte are produced, the catholyte containing hydrogen peroxide and the anolyte containing hypochlorous ions may be added to the water to be treated at one or both at a position upstream and downstream of the electrolytic cell.

While the invention has been described in detail and with reference to specific embodiments thereof, it will be apparent to one skilled in the art that various changes and modifications can be made therein without departing from the spirit and scope thereof.

This application is based on Japanese Patent Application No. 2001-85533 filed Mar. 23, 2001, the disclosure of which is incorporated herein by reference it its entirety.

What is claimed is:

1. An electrolytic cell for the production of hydrogen peroxide solution and hypohalide by electrolysis, which comprises an anode chamber housing an insoluble anode capable of oxidizing halide ion; a cathode chamber housing a gas diffusion cathode capable of oxidizing an oxygen-containing gas to produce hydrogen peroxide, said cathode chamber is partitioned by said gas diffusion cathode into a solution chamber and a gas chamber, a gas chamber is arranged on a side of the solution chamber opposite the anode chamber, and the electrolytic cell comprises means for supplying seawater to the solution chamber; a membrane separating the anode and cathode chambers; and means for supplying water containing halide ion to the anode chamber and an oxygen-containing gas to the gas chamber, whereby an anolyte containing hypohalide is produced in the anode chamber and a catholyte containing hydrogen peroxide is produced in the cathode chamber.

2. A process for the production of hydrogen peroxide solution and hypohalide which comprises removing organic material from seawater, and then electrolyzing the seawater in an electrolytic cell comprising an anode chamber housing an insoluble anode capable of oxidizing halide ion, a cathode chamber housing a gas diffusion cathode capable of oxidizing an oxygen-containing gas to produce hydrogen peroxide, and a membrane separating the anode and cathode chambers, while supplying the seawater treated to remove organic material to the anode chamber and an oxygen-containing gas and seawater either treated or untreated to remove organic material to the cathode chamber, to produce an anolyte containing hypohalide and a catholyte containing hydrogen peroxide.

3. The process as claimed in claim 2, wherein said cathode chamber is partitioned by said gas diffusion cathode into a solution chamber and a gas chamber, the gas chamber is arranged on a side of the solution chamber opposite the anode chamber, and said process comprises supplying seawater either treated or untreated to remove organic material to said solution chamber.

4. The process as claimed in claim 2, which comprises producing, as separate products, an anolyte containing hypohalide and a catholyte containing hydrogen peroxide.

5. The process as claimed in claim 2, which comprises producing an anolyte containing hypohalide and a catholyte containing hydrogen peroxide substantially free of effective chlorine.

6. A process for treating water which comprises electrolyzing a part of the water to be treated in an electrolytic cell comprising an anode chamber housing an insoluble anode capable of oxidizing halide ion, a cathode chamber housing a gas diffusion cathode capable of oxidizing an oxygen-containing gas to produce hydrogen peroxide, and a membrane separating the anode and cathode chambers, while supplying water containing halide ion to the anode chamber and an oxygen-containing gas and an electrolyte comprising the part of the water to be treated to the cathode chamber, to produce an anolyte containing hypohalide and a catholyte containing hydrogen peroxide, and then adding catholyte containing hydrogen peroxide and anolyte containing hypochlorous ion to the remainder of the water to be treated.

7. The process as claimed in claim 6, wherein said water to be treated is a water stream, and said catholyte containing hydrogen peroxide and said anolyte containing hypochlorous ion are fed to the water stream at one or both of a position upstream and downstream of the electrolytic cell.

8. The process as claimed in claim 6, wherein the cathode chamber is partitioned by said gas diffusion cathode into a solution chamber and a gas chamber, the gas chamber is arranged on side of the solution chamber opposite the anode chamber, and said process comprises supplying an electrolyte comprising the part of the water to be treated to said solution chamber.

9. The process as claimed in claim 6, which comprises producing, as separate products, an anolyte containing hypohalide and a catholyte containing hydrogen peroxide.

10. The process as claimed in claim 6, which comprises producing an anolyte containing hypohalide and a catholyte containing hydrogen peroxide substantially free of effective chlorine.

11. An electrolytic cell for the production of hydrogen peroxide solution and hypohalide by electrolysis, which comprises an anode chamber housing an insoluble anode capable of oxidizing halide ion; a cathode chamber housing a gas diffusion cathode capable of oxidizing an oxygen-containing gas to produce hydrogen peroxide, said cathode chamber is partitioned by said gas diffusion cathode into a solution chamber and a gas chamber, a gas chamber is arranged on a side of the solution chamber opposite the anode chamber, and the electrolytic cell comprises means for supplying seawater to the solution chamber; a membrane separating the anode and cathode chambers; means for supplying water containing halide ion to the anode chamber and an oxygen-containing gas and an electrolyte to the gas chamber; and means for producing, as separate products, an anolyte containing hypohalide in the anode chamber and a catholyte containing hydrogen peroxide in the cathode chamber.

12. The electrolytic cell as claimed in claim 11, which comprises means for producing an anolyte containing hypohalide in the anode chamber and a catholyte containing hydrogen peroxide substantially free of effective chlorine in the cathode chamber.

* * * * *